United States Patent
Olivera et al.

(10) Patent No.: US 6,438,202 B1
(45) Date of Patent: Aug. 20, 2002

(54) METHOD USING POST-PATIENT RADIATION MONITOR TO VERIFY ENTRANCE RADIATION AND DOSE IN A RADIATION THERAPY MACHINE

(75) Inventors: Gustavo H. Olivera; Jeffrey M. Kapatoes; Thomas R. Mackie; Paul J. Reckwerdt; Edward E. Fitchard; Julie C. Zachman, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/555,468

(22) PCT Filed: Aug. 6, 1999

(86) PCT No.: PCT/US99/17673

§ 371 (c)(1),
(2), (4) Date: May 30, 2000

(87) PCT Pub. No.: WO00/07667

PCT Pub. Date: Feb. 17, 2000

Related U.S. Application Data

(63) Continuation of application No. 10/038,379, filed on Jan. 4, 2002, which is a continuation of application No. 08/950,462, filed on Oct. 15, 1997, now Pat. No. 6,345,114, which is a continuation of application No. 08/490,184, filed on Jun. 14, 1995, now abandoned.

(51) Int. Cl.[7] ................................................. A61N 5/10
(52) U.S. Cl. ......................... 378/65; 378/152; 378/160
(58) Field of Search ........................ 378/65, 151, 152, 378/153, 4, 147, 150, 160

(56) References Cited

U.S. PATENT DOCUMENTS 5,394,452 A * 2/1995 Swerdloff et al. ............ 378/65
5,458,125 A * 10/1995 Schweikard .................. 378/65

FOREIGN PATENT DOCUMENTS

| EP | 0804943 | 5/1997 | ............ A61N/5/10 |
|----|---------|--------|----|
| EP | 0804943 A2 | 11/1997 | |

OTHER PUBLICATIONS

PCT Search Report issued in PCT/US99/17673, dated Dec. 2, 1999.

Todd R. McNutt et al., "Modeling dose distributions from portal dose images using the convolution/superposition method," *Medical Physics*, 23:1381–1392 (Aug. 1996).

V.N. Hansen et al., "The application of transit dosimetry to precision radiotherapy," *Medical Physics*, 23:713–721 (Feb. 1996).

Harald Keller et al., "Calibration of a portal imaging device for high–precision dosimetry: A Monte Carlo study," *Medical Physics*, 25:1891–1902 (Oct. 1998).

* cited by examiner

*Primary Examiner*—David P. Porta
*Assistant Examiner*—Therese Barber
(74) *Attorney, Agent, or Firm*—Quarles & Brady LLP

(57) ABSTRACT

In radiotherapy, a high quality imaging array may be placed after the patient and opposite the radiation source to be used during radiation treatment to verify operation of a shutter system or similar device and/or to compute dose delivered to the patient. A model of the patient may be used and inverted in order to estimate values of energy fluence prior to absorption by the patient and overlapping of the various radiation beams passing through the patient. A test pattern of shutter excitation to illuminate a single ray at a time provides a simple method of obtaining the necessary model. The dose from this test pattern may be subtracted from the subsequent radiation treatment so as to provide limited or no increase in total dose to the patient.

25 Claims, 4 Drawing Sheets

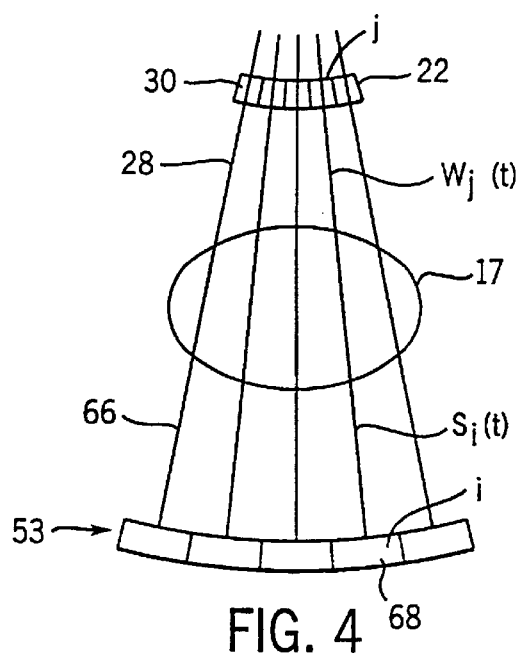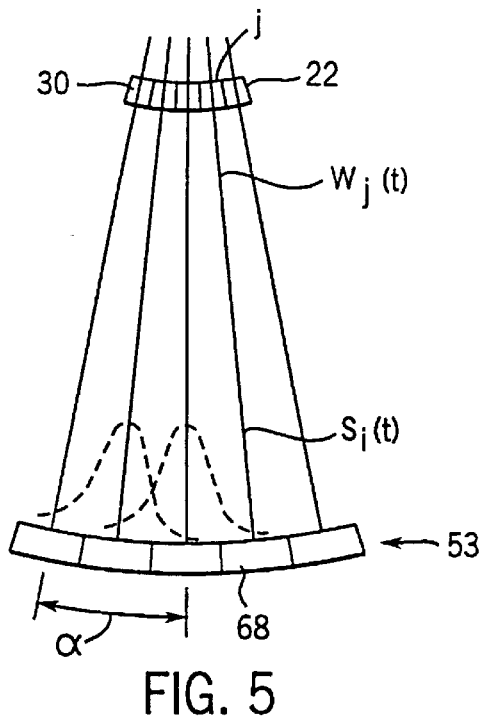
FIG. 4
FIG. 5
FIG. 6
FIG. 7

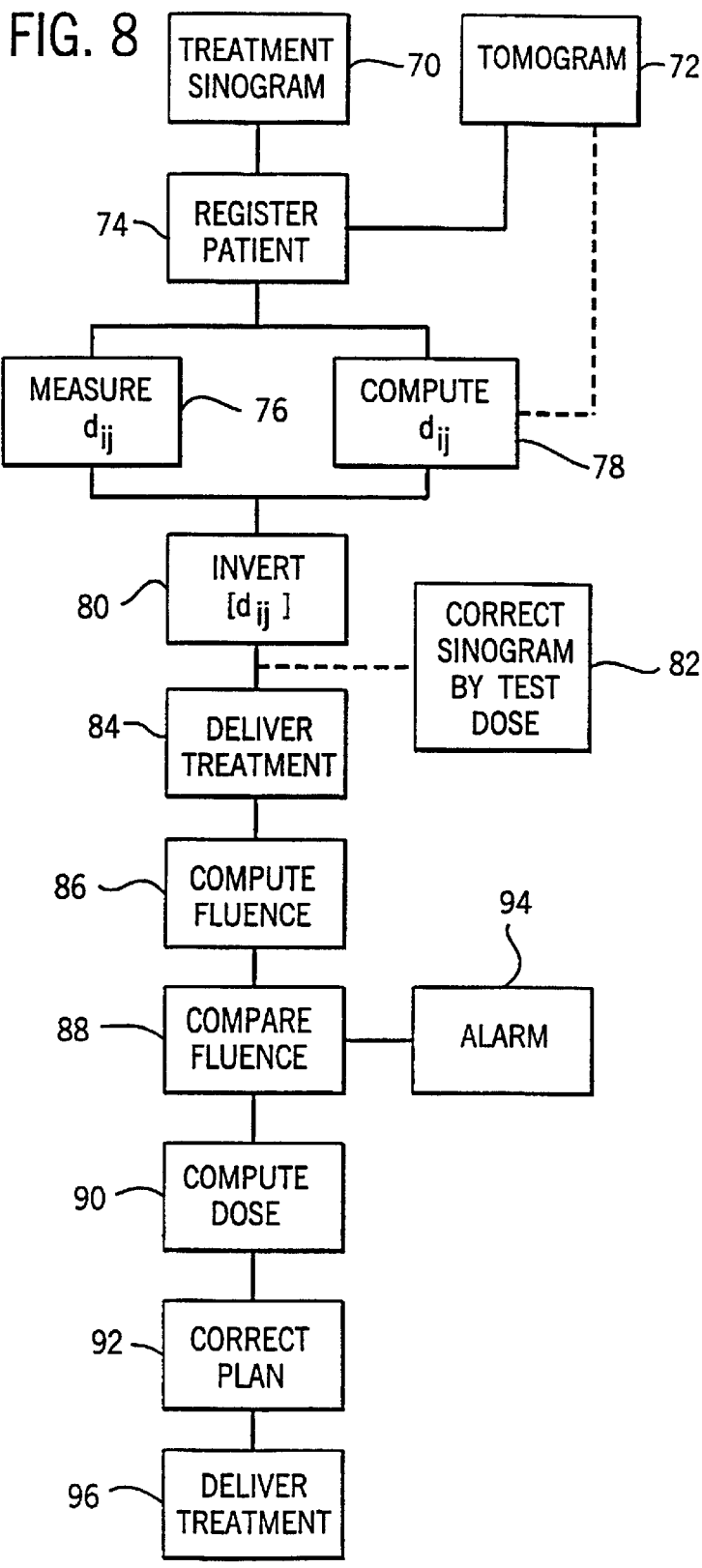
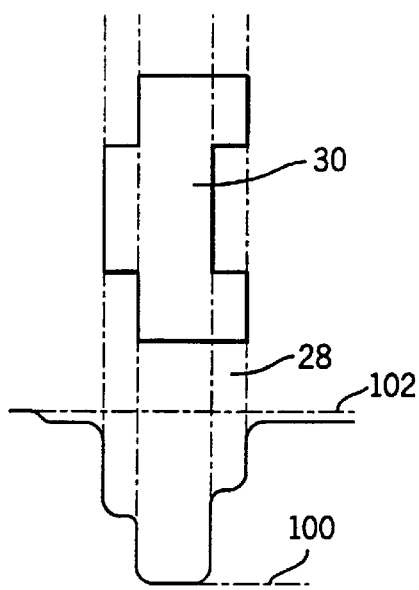
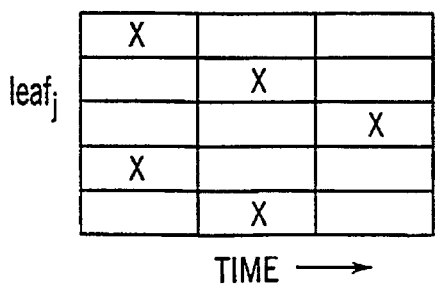

METHOD USING POST-PATIENT RADIATION MONITOR TO VERIFY ENTRANCE RADIATION AND DOSE IN A RADIATION THERAPY MACHINE

CROSS-REFERENCE TO RELATED APPLICATIONS

This application is a continuation of U.S. patent application No. 10/038,379 filed Jan. 4, 2002 which is a continuation of U.S. patent application No. 08/950,462 filed Oct. 15, 1997, now U.S. Pat. No. 6,345,114, which is a continuation of U.S. patent application No. 08/490,184 filed Jun. 14, 1995 abandoned.

BACKGROUND OF THE INVENTION

This invention relates generally to radiation therapy equipment for the treatment of tumors or the like and specifically to a radiation therapy machine allowing individual real-time control of the intensity of multiple rays within a treatment radiation beam.

Medical equipment for radiation therapy treats tumorous tissues with high energy radiation. The amount of radiation and its placement must be accurately controlled to ensure both that the tumor receives sufficient radiation to be destroyed and that the damage to the surrounding nontumorous tissue is minimized.

One highly accurate method of controlling the dose to a patient employs a radiation source that produces a radiation beam composed of many individual rays whose intensity may be individually controlled. This beam may be produced by a series of shutters, each controlling one ray, or by a single modulated ray moving across the patient to create the beam over an interval of time.

The origin of the rays moves over a range of angles about the patient and by properly selecting the ray intensities at different angles, complex regions within the patient may be accurately irradiated. U.S. Pat. Nos. 5,724,400; 5,673,300; 5,668,371; 5,661,773; 5,625,663; 5,548,627; 5,528,650; 5,442,675; 5,394,542; and 5,317,616, all assigned to the same assignee as the present application, and hereby incorporated by reference, describe the construction of a machine of this type and a method of calculating the necessary ray intensities as a function of angle. In the described machine, shutters switched between open and closed states each control the intensity of a corresponding individual ray, however other methods are also known of delivering rays of varying intensities including those using a single modulated and scanning ray and other such systems.

The promise of improved accuracy of such radiation therapy systems and their increased complexity make it desirable to have a means of verification of the correct operation of the shutters and thus the intensity of the rays irradiating the patient. A post-patient radiation monitor, commonly known as an "exit detector", may provide an approximate indication of the correct operation of the radiation therapy machine, but patient attenuation, scatter, and the overlap of rays at detector elements of the post-patient radiation detector prevent the direct observation of shutter operation in a post-patient image. Nevertheless, the sensitivity of the post-patient radiation monitor to attenuation of radiation by the patient allows it to be used for imaging of the patient for registration and verification of patient positioning or the like with the shutters fully open.

Indirect verification of intensity may be provided by cameras viewing the shutters or sensors mounted on the shutters to indicate their correct operation and movement. Information about shutter operation together provides a general indication of the fluence of the rays directed toward the patient provided profile of the radiation beam incident on the shutters is known and reliable.

Preferably and as taught in U.S. Pat. No. 5,394,452 cited above, a pre-patient radiation monitor may be used to make direct measurement of the intensity of the rays. The pre-patient monitor provides a measurement of fluence received by the patient but is cumbersome and unlike a post-patient radiation monitor cannot be used to provide information about patient positioning or imaging.

BRIEF SUMMARY OF THE INVENTION

The present inventors have recognized that a post-patient monitor alone may in fact be used to verify operation of the shutter system during radiation therapy on a particular patient if the response of the patient attenuation and ray paths can be accurately modeled. The model can then be inverted and applied to the detected radiation exiting the patient to give an indication of the entrance fluence of the individual rays or other related physical quantities such as energy. The entrance fluence together with some information about the patient, from a tomogram of the like, can be used to deduce the dose delivered to the patient.

The model may be constructed from a known geometry of the radiation therapy machine and estimated properties of the patient or standard patient, or properties of the patient as deduced from a pre-treatment tomogram or from an experimental or theoretically derived database, or may be derived by a selective excitation of different shutters and measurements of the received signals immediately prior to or during the radiation treatment session. The radiation used in such measurements may be "borrowed" from the treatment plan itself so as to leave the total dose to the patient unaffected.

Specifically, the invention provides a method of verifying operation of a radiotherapy radiation source in a radiotherapy machine operable to produce multiple rays of radiation having controllable fluence. The rays are directed across a patient volume to a detector of multiple detector elements which provide detector signals at spatially separate points, each detector element receiving radiation from multiple rays. The steps include receiving a treatment plan to operate the radiation source to produce a set of rays of predetermined fluence and operating the radiotherapy machine according the received treatment plan. Concurrently with the radiation therapy, detector signals are measured and processed using a model of the expected attenuation of each ray passing from the radiation source through the patient volume to the detector to deduce a measured fluence of each of the set of rays. Finally, the measured fluence is compared to the predetermined fluence of each ray to verify operation of the radiation source or to deduce the dose applied to the patient.

Thus it is one object of the invention to provide a radiation therapy system requiring only a single post-patient radiation monitor. Because the radiation monitor is not interposed between the patient and the radiation source, it may be in part or wholly absorbent providing greater flexibility in design. Unlike a pre-patient monitor, the post-patient monitor may be used for patient imaging and positioning tasks.

The model may be based on known geometry of the radiation therapy system optionally augmented by tomographic information about the patient. Alternatively, the model may be produced from a series of measurements of the patient or a phantom in which the radiation source is operated to produce a predetermined sequence of test fluences for the set of rays and those fluences used to produce a model. The data may be stored in a database and optionally sets of data combined to produce data for a standard patient.

Thus it is another object of the invention to provide a verification system that accurately accounts for modification of the beam as it passes through the patient.

The predetermined sequence of test fluences for the set of rays may provide a unit fluence for one ray at a time to create an impulse response of the patient/radiation source.

Thus it is another object of the invention to provide a simple method of characterizing the patient and the radiation path such as may be used for verification of radiation source output and/or dose by a post-patient radiation detector.

Multiple sets of rays may be simultaneously energized to the unit fluence in the predetermined sequence provided the rays do not overlap at the detector or overlap minimally.

Thus it is another object of the invention to provide a rapid method of acquiring the necessary data for the model used for verification.

The radiation treatment plan may be modified to subtract the fluences of the predetermined sequence of test fluences thereby leaving the dose to the patient unincreased.

Thus it is another object of the invention to provide extremely accurate characterization of the patient using the actual radiation used for treatment while avoiding the penalty of increased dose to the patient.

The predetermined sequence may provide a unit fluence only for rays actually used in the radiation treatment plan. Estimates may be made for those rays not so measured.

Thus it is another object of the invention to provide accurate modeling of the patient only for rays whose dose may be "borrowed" from other portions of the radiation plan preventing the increase of total dose to the patient.

It is another object of the invention, therefore, to provide some information for verification of rays that are not expected to be used in the radiation therapy system in order to track possible errors in which they would be open.

The treatment plan may include multiple sessions and the method may provide for correcting of the treatment plan to account for deviations between the measured fluence and the predetermined fluence for subsequent sessions.

Thus it is another object of the invention to accommodate minor errors in treatment through corrective action on subsequent treatments.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

BRIEF DESCRIPTION OF THE DRAWINGS

FIG. 4 is a simplified representation of the gantry of the radiation therapy machine of FIG. 3 showing variables used in the calculation of a patient model;

FIG. 5 is a figure similar to that of FIG. 4 showing complications in the determination of entrance fluence at a post-patient radiation detector caused by overlapping of the radiation of different rays at the post-patient radiation detector;

FIG. 6 is a table showing a shutter actuation pattern such as provides test fluences for measuring an impulse response of the patient/shutter system suitable for deriving a model of the patient shutter system;

FIG. 7 is a figure similar to that of FIG. 6 providing a more complex shutter actuation pattern to provide a model better accounting for penumbra and other nonlinearities;

FIG. 8 is a flow chart of the steps of the present method in verifying, modeling and correcting a radiation therapy session;

FIG. 9 is an exaggerated view of one shutter of FIG. 2 showing tongue and groove and penumbra effects; and FIG. 10 is a figure similar to that of FIG. 6 showing a shutter actuation pattern providing a rapid method generating a model of the patient/shutter system.

DETAILED DESCRIPTION OF THE INVENTION

Figure 1:
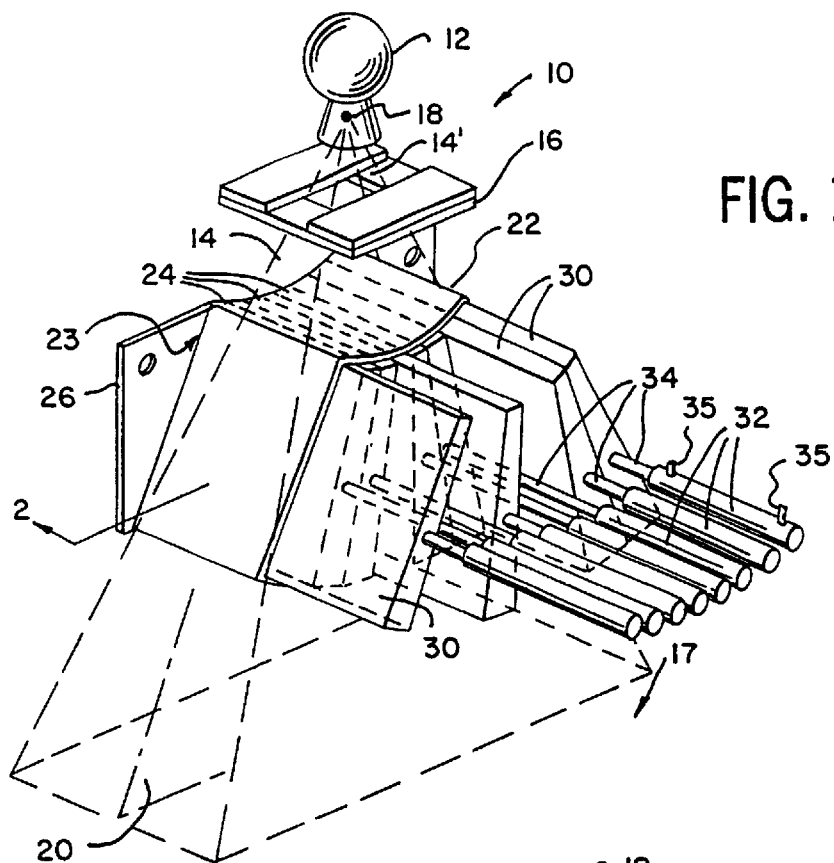
FIG. 1 is a perspective view of the shutter system assembly used in the present invention showing the shutter leaves and their associated electromagnetic actuators.

Referring to FIG. 1, a radiation therapy machine 10 suitable for use with the present invention includes a radiation source 12 producing a generally conical radiation beam 14' emanating from a focal spot 18 and directed toward a patient 17 (not shown in FIG. 1). The conical radiation beam 14' is collimated by a rectangular opaque mask 16 constructed of a set of rectangular shutter system blades to form a generally planar radiation fan beam 14 centered about a radiation fan beam plane 20.

A shutter system 22 is centered in the radiation fan beam 14 and about the radiation fan beam plane 20 prior to the radiation beam being received by the patient 17, and includes a plurality of adjacent trapezoidal leaves 30 which together form an arc of constant radius about the focal spot 18. Each leaf is constructed of a dense radio-opaque material such as lead, tungsten, cerium, tantalum or related alloy.

The leaves 30 are held in sleeves 24 so that each leaf 30 may slide completely within its corresponding sleeve 24 to block the ray 28 associated with that sleeve 24. Preferably, the leaves 30 of the shutter system 22 subtend the entire radiation fan beam to divide the radiation fan beam into a set of adjacent slab-like rays 28 at offset angles φ. When the leaf 30 blocks its corresponding ray 28, it is referred to as being in the closed state. The sleeves 24 are of ample length to permit each leaf 30 to slide out of the path of the radiation fan beam so as to leave its corresponding ray 28 completely unobstructed and yet to still be guided by the sleeve 24. In this nonlocking position, a leaf is referred to as being in the "open state".

Each leaf 30 may move rapidly between its open and closed state by means of a primary relay-like electromagnetic actuator 32 connected to the leaf 30 by a slider member 34. The fluence passed by the ray 28 may be controlled by changing the duty cycle of the movement of the leaf that is the ratio of time between which it is in the open state as opposed to the closed state.

Figure 2:
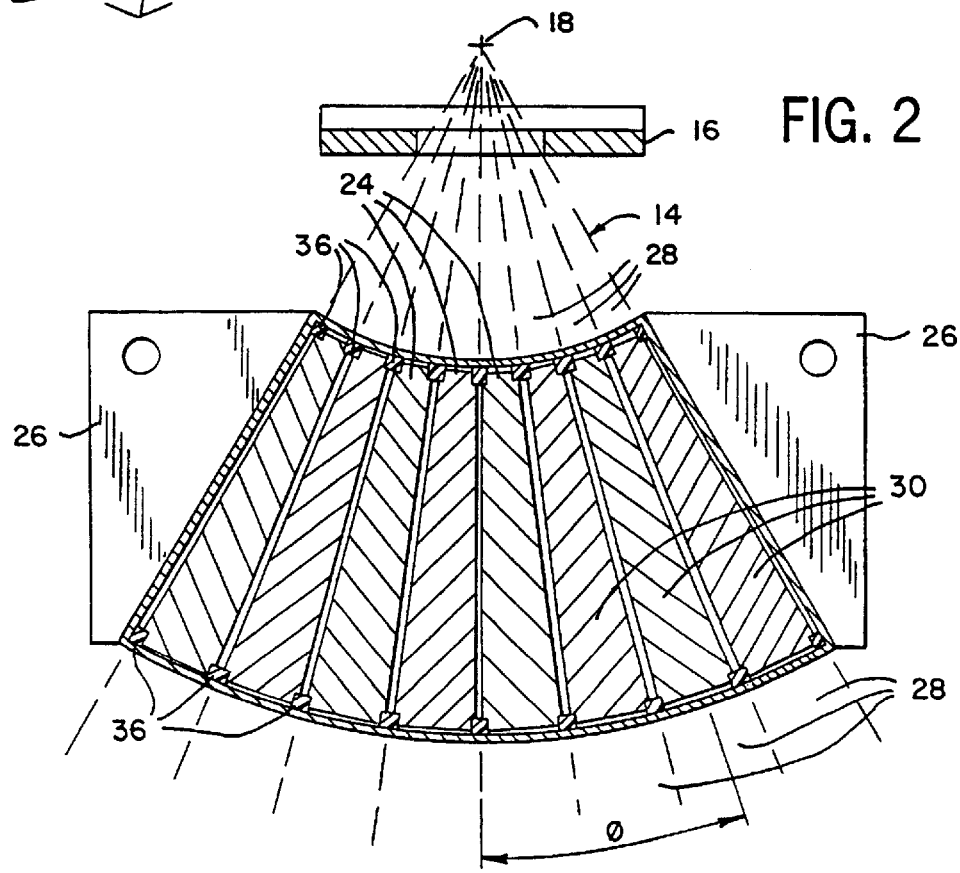
FIG. 2 is a cross section of the shutter system of FIG. 1 along line 2—2 showing the trapezoidal aspect of each shutter leaf for a radiation fan beam of radiation, and the guide rails for supporting the shutter leaves when they move.

Referring to FIG. 2, the leaves 30 are supported and guided within the sleeves 24 by guide tongues 36 fitted into grooves 38 cut along the edges of the leaves 30. The grooves 38 allow the guide tongues 36 to slidably retain the leaves 30 within the sleeves 24 during motion between the open and closed states.

Figure 3:
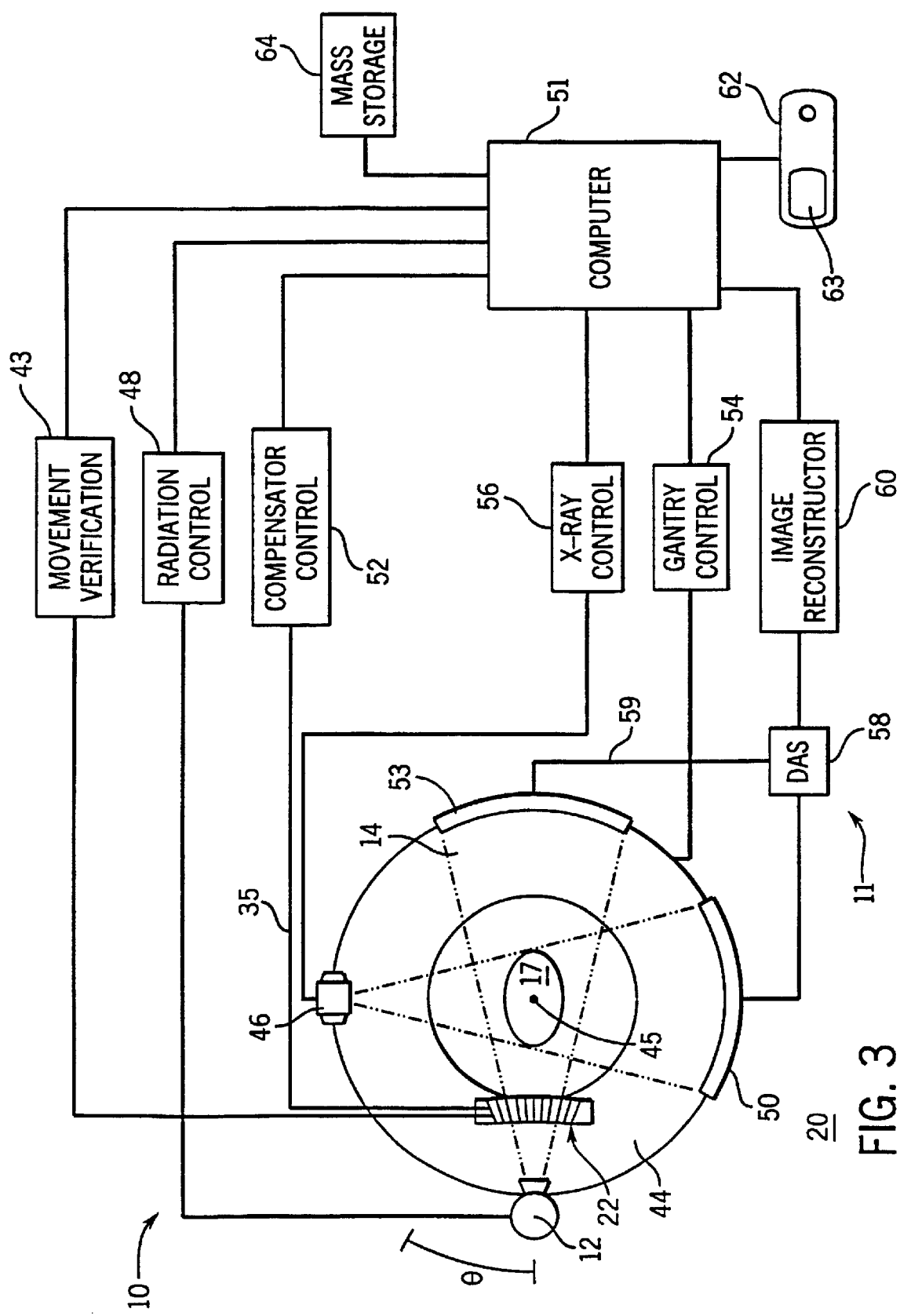
FIG. 3 is a block diagram showing the elements of a radiation therapy machine incorporating a conventional CT scanner and the shutter system of the present invention and including a computer suitable for controlling that shutter system per the present invention.

Referring now to FIG. 3, the radiation source 12 is mounted on a gantry 44, the latter rotating within the radiation fan beam plane 20 about a center of rotation 45 in the patient 17 so that the radiation fan beam 14 may irradiate a slice of the patient 17 from a variety of gantry angles θ. The radiation source 12 is controlled by a radiation control module 48 which turns the radiation beam 14 on or off under the control of a computer 51.

A shutter system control 52 directed by a timer generating desired position signals provides electrical excitation to each electromagnet to control, separately, the actuators 32 to move each of the leaves 30 in and out of its corresponding sleeve 24 and ray 38 (see also FIG. 1). Alternatively a pneumatic system can be used. The shutter system control 52 moves the leaves 30 of the shutter system 22 rapidly between their open and closed states to either fully attenuate or provide no attenuation to each ray 28. Gradations in the fluence of each ray, as needed for the fluence profile, are obtained by adjusting the relative duration during which each leaf 30 is in the closed position compared to the relative duration during which each leaf 30 is in the open position for each gantry angle.

It will be understood from the following description, however, that the present invention is not limited to a one dimensional shutter system but may be used in any radiation therapy machine which allows independent modulation of a series of rays of radiation directed through the patient either simultaneously or over an interval of time. Thus, two dimensional shutter systems, wedge type shutters or even electronic modulation of the beam is suitable for use with the invention.

The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below. The shutter system control 52 also connects with computer 51 to allow program control of the shutter system 22 to be described.

An optional tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planing purposes. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the gantry angle θ of the radiation fan beam 14 for the radiation therapy, as well as for the computer tomography x-ray source 46 and detector array 50 also attached to gantry 44. Gantry control module 54 connects with computer 51 so that the gantry may be rotated under computer control and also to provide the computer 51 with a signal indicating the gantry angle θ to assist in that control.

Control modules for the tomographic imaging system 11 include: x-ray control module 56 for turning on and off the x-ray source 46 and data acquisition system 58 for receiving data from the detector array 50 n order to construct a topographic image.

An image reconstructor 60 typically comprising a high speed array processor or the like receives data from the data acquisition system 58 in order to assist in "reconstructing" a tomographic treatment image from such data according to methods well known in the art. The image reconstructor 60 may also use post-patient radiation detector signals 59 to produce a tomographic absorption image to be used for verification and future therapy planning purposes as described in more detail below.

A terminal 62 comprising a keyboard and display unit 63 allows an operator to input programs and data to the computer 51 and to control the radiation therapy machine 10 and the tomographic imaging system 11 and to display images provided by the image reconstructor 60 on display unit 63.

A mass storage system 64, being either a magnetic disk unit or tape drive, allows the storage of data collected by the tomographic imaging system 11 and the post-patient radiation detector 53 for later use. Computer programs for operating the radiation therapy machine 10 will generally be stored in mass storage system 64 and loaded into the internal memory of the computer 51 for rapid processing during use of the radiation therapy machine 11.

The radiation source 12 may be a linear accelerator excited in pulsed mode with the pulses in synchrony with the digital to analog converter of the data acquisition system 58 so a set of views may be obtained during shutter opening and closing. As a non-limiting example, if each projection of radiation at a given gantry angle θ during radiotherapy is one second, the pulse rate of the linear accelerator may be two hundred times per second providing real-time motion study of movement of the leaves 30 based on the changing fluence exiting the leaf and entering the patient 17.

During operation of the radiation therapy machine 11, the shutter system control 52 receives from the computer 51 a treatment sinogram comprising a fluence profile for each gantry angle θ. The treatment sinogram describes the intensity or fluence of each ray 28 of the radiation beam 14 that is desired for each gantry angle θ at a given position of the patient support table (not shown) as translated through the radiation beam 14.

Referring now to FIG. 4, a shutter system provides control of a total number J of rays 28 identified by index variable j=1 to J. Each ray 28 generated by the shutter system 22 passes through the patient 17 along ray center line 66 to be detected by post-patient radiation detector 53 having I detector elements identified by index variable i=1 to I. Each detector element produces a signal $S_i(t)$ related to one detector element i. The signal may indicate fluence, energy or any related physical quantity.

Monitoring the operation of the shutter system 22 by means of post-patient radiation detector 53 is complicated by the attenuation produced by the patient 17 along ray center line 66. Thus if the fluence received by the post-patient radiation detector 53 appears to vary from that demanded by the treatment sinogram, a determination must also be made as to whether the shutter system 22 is misfunctioning or whether the attenuation of the patient 17 is other than that anticipated. Therefore it will be understood that the system can be used to detect patient motion provided that the entrance fluence or correct operation of the shutters is gathered in some other way.

Referring to FIG. 5, a second complication of using the post-patient radiation detector 53 for monitoring the shutter system 22 is that the rays 28 in fact subtend an angle α about their center line 66 typically greater than the desired size of a single detector element of post-patient radiation detector 53. Thus each detector element receives radiation from multiple rays and an attempt to determine whether a given leaf i of the shutter system 22 is properly functioning can require knowledge of the state of other leaves.

The present inventors have recognized that both of these complicating circumstances may nevertheless be overcome by a modeling of the attenuation of the patient 17 and the geometry describing the relationship between the shutter system 22 and the post-patient radiation detector 53 specifically in the form of a set of simultaneous equations.

As above, assuming that there are J leaves 30 and I detector elements 68, then generally, the signal $S_i(t)$ received by detector element i at a time t can be written as:

$$S_i(t)=d_{i1}w_1(t)+d_{i2}w_2(t)+d_{i3}w_3(t)+ \ldots +d_{iJ}w_J(t) \quad (1)$$

where $d_{i,j}$ represents the signal that would be acquired at the detector element i for one unit of energy fluence delivered by a leaf j and $w_j$ represents the total fluence exiting the shutter system 22 at leaf j. Note generally that the signal $S_i(t)$ for each detector element i is a function of multiple rays and a function of the attenuation properties of the patient 17.

The $d_{ij}$ values can be considered as a set of responses of the system due to impulse functions produced by the different leaves 30. To a first order, the main dependence of elements $d_{ij}$ will be on the radiological path length through the patient from the shutter system 22 to the post-patient radiation detector 53. For any given angle of the gantry θ about the patient, $d_{ij}$ can be considered time independent. The signal of the complete set of detector elements 68 can be written in matrix form as:

$$\begin{bmatrix} S_1(t) \\ S_2(t) \\ \hline S_i(t) \\ \hline S_I(t) \end{bmatrix} = \begin{bmatrix} d_{11}(t) & d_{12}(t) & d_{1j}(t) & d_{1J}(t) \\ d_{21}(t) & d_{22}(t) & d_{2j}(t) & d_{2J}(t) \\ \hline d_{i1}(t) & d_{i2}(t) & d_{ij}(t) & d_{iJ}(t) \\ \hline d_{I1}(t) & d_{I2}(t) & d_{Ij}(t) & d_{IJ}(t) \end{bmatrix} \begin{pmatrix} w_1(t) \\ w_2(t) \\ w_j(t) \\ w_J(t) \end{pmatrix} \quad (2)$$

This may be written in simplified notation as:

$$\overline{S}(t)=[\overline{d}_{ij}(t)]\overline{w}(t) \quad (3)$$

In a typical configuration, the matrix of $d_{ij}$ values will be a sparse non-square matrix. Therefore, a pseudo inverse of the matrix may be obtained so as to compute the values of $w_j(t)$ based on a knowledge of the signals $S_i(t)$ received by the post-patient radiation detector 53. Thus if elements $d_{ij}$ can be obtained and the system is linear and its inverse can be computed, the operation of the shutter system 22 may be verified by the signals $S_i(t)$ from the post-patient radiation detector 53 to supplement or be used instead of other verification mechanisms.

Generally therefore:

$$\overline{w}(t)=[\overline{d}_{ij}(t)]^{-1}\overline{S}(t) \quad (4)$$

Referring now to FIG. 6, the matrix $[\overline{d}_{ij}(t)]$ provides a model of the patient/shutter system and may be produced by (1) making assumptions about the patient 17 and incorporating the known parameters of the geometry of the radiation therapy machine, or (2) actually measured, or (3) a combination of these two approaches.

In one embodiment, the matrix $[\overline{d}_{ij}(t)]$ is obtained using a phantom approximating a patient and irradiated to measure the values of matrix $[\overline{d}_{ij}(t)]$ as will be described below. The matrix $[\overline{d}_{ij}(t)]$ is then stored and adapted to the patient according to gross differences between the patient and the phantom. Alternatively, the matrix $[\overline{d}_{ij}(t)]$ may be obtained while the patient is in place on the radiation therapy machine.

In either case, measurement of the values of $d_{ij}$ may be obtained by individually energizing each leaf 30 in sequence so that only one leaf 30 is open at a given time as indicated by the timing chart of FIG. 6 which shows an opening as cells having an x. For each open leaf, one column of the matrix $d_{ij}$ values is obtained as may be understood from inspection of the above equations by noting that a single leaf corresponds to the w vector as having a single nonzero value. This process may be repeated for each gantry angle θ so that a number of matrices $d_{ij\theta}$ may be found and their inverses used at different times during the radiation therapy to apply to the receive signals $S_i(t, \theta)$ according to the particular gantry angle θ at which the signals are received. The matrix of $d_{ij\theta}$ values will accommodate both the attenuating properties of the patient 17 referred to above with respect to FIG. 4 and the interaction between the rays and detector elements as referred to above with respect to FIG.

5. Preliminary studies indicate that as few as three pulses of the linear accelerator are enough to measure $d_{ij}$.

Referring then to FIG. 8, a radiation therapy session may begin with the receipt of a treatment sinogram 70 as indicated by like numbered process block 70. At the same time, a tomogram 72 of the patient may be taken as indicated by like numbered process block 72 making use of the detector array 50 and x-ray source 46 described above.

The tomogram may be used to properly register the patient 17 on the radiation therapy machine as indicated by process block 74, either by moving the patient 17 on a support table or the like or modifying the treatment sinogram 70 to conform with the moved patient.

Typically a treatment sinogram 70 will result in certain leaves 30 at certain angles θ not being opened. In a preferred embodiment, only for those leaves which are opened is a measurement of $d_{ij}$ values made, as indicated by process block 76. As described above, the leaves that will be opened during treatment are opened one at a time providing measurements of columns of the matrix $[\overline{d}_{ij}(t)]$ above.

As indicated by process block 78 in parallel with process block 76, for those leaves which are not opened during therapy and yet which a $d_{ij}$ value may be desired, $d_{ij}$ values may be estimated or modeled either using comparable $d_{ij}$ values obtained with a phantom positioned in lieu of the patient 17, for example, a water phantom representing an average attenuation property of the patient, or by making use of the information derived from the tomogram 72. Such $d_{ij}$ values may be used for the purpose of monitoring the normally closed leaves 30 against possible accidental opening. Estimates of this kind may also be obtained to reduce the time required to obtain the $d_{ij}$ values or to reduce the dose to the patient 17.

In the case using a phantom to model the patient 17, this requires simply the performance of the steps of opening individual leaves per process block 76 but with a phantom in place and storing those values for later use. Pure modeling may be done by using Monte Carlo or other techniques on a standard patient or the acquired data of tomogram 72.

At succeeding process block 80, the matrix $[\overline{d}_{ij}(t)]$ is inverted for use in monitoring the operation of the shutter system 22. At an optional process block 82, the dose delivered to the patient 17 in the process of measurement of $d_{ij}$ values per process block 76 may be subtracted from the treatment sinogram 70 so as to result in no net increase in dose to the patient as a result of this process. The use of modeling of process block 78 for leaves which are normally not opened facilitates this ability to eliminate extra dose.

At process block 84, the radiation therapy treatment is delivered with a monitoring of the signals $S_i(t)$ from the post-patient radiation detector 53 at each gantry angle θ applied against an inverted matrix $[\overline{d}_{ij}(t)]$ selected according to the gantry angle θ. Dark current may be subtracted from the signals $S_i(t)$ prior to further processing.

At process block 86, this fluence w(t) is computed using the inverted matrices $[\overline{d}_{ij}(t)]^{-1}$ and at process block 88, the computed fluence is compared to the fluence dictated by the treatment sinogram 70 possibly as modified by process block 82.

At process block 90, dose delivered to the patient 17 is computed using the measured fluence determined at process block 86. If the measured fluence is less than that anticipated by the treatment sinogram 70, then at process block 92, later stages (gantry angles θ) of the treatment may be corrected, or in the case where the treatment sinogram is delivered in multiple sessions, later sessions of the treatment sinogram may be compensated to correct for a shortfall or overage of dose.

If there is a consistent error in fluence, an alarm output may be provided to the operator as indicated at process block 94 indicating a problem with one or more leaves 30. Likewise, leaf performance may be monitored for trends such as may indicate a potential failure and detection of these trends may also result in an alarm condition.

At process block 96, the radiation treatment plan is continued and the process may loop back to process block 84.

Referring now to FIG. 9, the assumption of linearity in the operation of the leaves 30 may be affected by a tongue and groove/penumbra (TAG-P) effect of the leaves 30. With a given leaf 30 in a closed position, a signal received along a central axis of the leaf will be at a first low value 100 corresponding to leakage through the leaf 30, scatter (mainly from primary collisions) and dark current of the post-patient radiation detector 53. At the edges of the ray 28, however, the signal will rise to a higher level 102 as a result of greater leakage through edges of the leaf 30 which incorporate a groove for support of the leaf 30 (on a corresponding fixed guide tongue 36 described above) and because of penumbra effects well known to those in the field of optics. It follows that it is not equivalent to an amount of energy fluence by one leaf at a time as opposed to several leaves simultaneously.

This deviation from linearity may be accommodated and corrected for by empirical measurements taken on a phantom or the like evaluating measurement with all leaves open versus one leaf at a time to identify the detector elements of the post-patient radiation detector 53 at the interfaces between leaves 30 thus most susceptible to the penumbra effect. This measurement may also determine a ratio by which signal 102 exceeds signal 100. This correction can be obtained by modeling also and correction may be iterative. Information obtained during the registration of the patient or the CT scan may also be used to account for these non-linearities.

At process block 86, the measured fluence may be used to provide a rough measure of which leaves 30 are open and which are closed and based on this determination, the ratio may be applied to the signals $S_i(t)$ of the relevant detectors identified as being subject to TAG-P effects when the spatial resolution of the detector elements is much finer than that provided by the leaves 30.

Higher order effects caused by TAG-P may be corrected by a more complex acquisition of the $d_{ij}$ matrix. Referring to FIG. 7, individual leaves 30 may be energized together with combinations of their neighbor leaves 30 so as to create a more complete database reflecting the interaction between leaves 30 on the detected signals. The information of this database may be applied again by making an initial determination of which leaves are open and closed ignoring the TAG-P effects and then applying the appropriate $d_{ij}$ matrix corresponding to that known state.

The leakage and transmission are implicitly incorporated into the measurement made at process block 76. However, this is an overcorrection when all leaves are open and there is no leakage or transmission to be considered. A correction of this may weight the value of $S_i(t)$ to decrease it as more leaves are open. A simple correction is to subtract the value corresponding to leakage and transmission from the different columns.

Referring now to FIG. 10, the acquisition of the measurement of $[\overline{d}_{ij}(t)]$ at process block 76 may be speeded by opening multiple shutters for rays 28 sufficiently far in separation from each other that they do not overlap appreciably. As shown in FIG. 10, every third leaf is open to reduce the total amount of time required for acquiring $[\overline{d}_{ij}(t)]$. Generally further increases in acquisition time may be obtained by making fewer actual measurements of leaves and estimating greater numbers of leaves based possibly on the measured leaves. Adjacent leaves may also be simultaneously opened and the overlap corrected by deconvolution using modeling.

The above description is applicable to systems in which the gantry is positioned at a series of discrete gantry angles θ about the patient (or in which the gantry position may be approximated by discrete gantry angles) while treatment is performed, thus leading to a limited number of discrete matrices $d_{ij\theta}$. It will be understood, however, that it may be preferable to provide for continuous gantry motion with or without continuous motion of the patient through the gantry, the latter providing a helical scanning pattern. In this case, the $d_{ij\theta}$ may represent average positions within a span of angles Δθ and locations z with respect to the patient or averages of multiple readings within that span Δθ.

The above description has been that of a preferred embodiment of the present invention, it will occur to those that practice the art that many modifications may be made without departing from the spirit and scope of the invention. In order to apprise the public of the various embodiments that may fall within the scope of the invention, the following claims are made.

We claim:

1. A method of verifying patient dose in the operation of a radiotherapy machine having a radiation source operable to produce multiple rays of radiation having controllable fluence and directed across a patient volume to be received by a detector having multiple detector elements providing detectors signals at spatially separated points, each detector element receiving radiation from multiple rays, the method comprising the steps of:
   (a) receiving a treatment plan to operate the radiation source to produce a set of rays of predetermined fluence;
   (b) operating the radiotherapy machine according to the received treatment plan;
   (c) concurrently with step (b) measuring the detector signals;
   (d) processing the detector signals using a model of the expected attenuation and path of each ray passing from the radiation source through the patient volume to the detector to deduce a fluence of each of the set of rays; and
   (e) using the deduced fluence and information about the structure of a patient in the patient volume to determined a dose distribution to the patient.

2. The method of claim 1 wherein the model is based on a standard patient and a known geometry of the path of the rays from the radiation source through the patient volume to the detector.

3. The method of claim 1 wherein the model is based on a phantom and a known geometry of the path of the rays from the radiation source through the phantom to the detector.

4. The method of claim 1 wherein the model is based on a tomogram of the patient and a known geometry of the path of the rays from the radiation source through the phantom to the detector.

5. The method of claim 1 further including the step of:
   (f) acquiring a tomogram indicating radiation absorption of a patient in the patient volume; and
   (g) wherein the information about the structure of a patient in the patient volume is obtained from the tomogram.

6. The method of claim 1 further including the step of:
   (f) operating the radiation source to produce a predetermined sequence of test fluences for the set of rays;
   (g) concurrently with step (f) measuring the detector signals; and
   (h) processing the detector signals of step (g) to produce the model of the expected attenuation of each ray passing from the radiation source through the patient volume to the detector.

7. The method of claim 6 wherein the predetermined sequence of test fluences for the set of rays of step (f) includes the step of providing a unit fluence for one ray at a time to create an impulse response of the patient volume at the detector.

8. The method of claim 6 wherein the predetermined sequence of fluences for the set of rays of step (f) includes the step of providing a unit fluence for multiple rays at a time, the multiple rays selected such that the multiple rays do not substantially overlap at the detector to create simultaneous multiple impulse responses of the patient volume at the detector.

9. The method of claim 6 including prior to step (b) the step of modifying the treatment plan to subtract the fluences of the predetermined sequence of fluences of step (f) thereby leaving the dose to the patient unincreased.

10. The method of claim 6 wherein step (f) of operating the radiation source to provide the predetermined sequence of fluences for the set of rays provides a unit fluence for one ray at a time for non-adjacent rays and including the step (i) of estimating the fluence of the rays not in the predetermined sequence.

11. The method of claim 6 wherein the model in an inverted matrix of elements $\overline{d}_{ij}$ derived from the test fluences and wherein the measured fluences w(t) are determined according to the formula:

$$w(t) = [\overline{d}_{ij}(t)]^{-1} \overline{S}(t)$$

where $\overline{S}(t)$ are measured detector signals of step (c).

12. The method of claim 6 wherein the predetermined sequence of test fluences includes only rays used in the treatment plan.

13. The method of claim 12 including the step of estimating the fluence of the rays not in the predetermined sequence of test fluences.

14. The method of claim 6 wherein the predetermined sequence of test fluences is repeated for a plurality of angles about the patient volume.

15. The method of claim 6 wherein the radiation plan provides for rays directed at a plurality of angles about the patient volume and wherein steps (b)–(d) are repeated for each angle of the radiation plan.

16. The method of claim 1 wherein the radiation treatment plan is based on a desired dose map indicating desired dose in different regions of a patient and including the further steps of:

(e) acquiring a radiation absorption tomogram of the patient;

(f) modeling actual dose received by the patient using the tomogram and the measured fluence; and (g) comparing the modeled actual dose against the dose map to evaluate the treatment.

17. The method of claim 1 wherein the treatment plan includes multiple sessions and including the step of:

(e) after a first session correcting the treatment plan to account for deviation between the measured fluence and the predetermined fluence; and (b) operating the radiotherapy machine according to the corrected treatment plan for a subsequent session.

18. A method of verifying operation of a radiotherapy shutter system in a radiotherapy machine having a radiation source positioned behind the shutter system, the shutter system operable to produce multiple rays of radiation having controllable fluence and directed across a patient volume to be received by a detector having multiple detector elements providing detectors signals at spatially separated points, each detector element receiving radiation from multiple rays, the method comprising the steps of:

(a) receiving a treatment plan to operate the shutter system to produce a set of rays of predetermined fluence;

(b) operating the radiotherapy machine according to the received treatment plan;

(c) concurrently with step (b) measuring the detector signals;

(d) processing the detector signals using a model of the expected attenuation and path of each ray passing from the shutter system through the patient volume to the detector to deduce a measured fluence of each of the set of rays; and (e) comparing the measured fluence to the predetermined fluence of each ray to verify operation of the shutter system.

19. The method of claim 18 wherein the predetermined sequence of test fluences for the set of rays of step (a) includes the step of providing a unit fluence for one ray at a time to create an impulse response of the patient volume at the detector.

20. The method of claim 19 wherein the predetermined sequence of fluences for the set of rays of step (a) includes the step of providing a unit fluence for multiple rays at a time, the multiple rays selected such that the multiple rays do not substantially overlap at the detector to create simultaneous multiple impulse responses of the patient volume at the detector.

21. The method of claim 18 including prior to step (d) the step of modifying the treatment plan to subtract the fluences of the predetermined sequence of test fluences of step (a) thereby leaving the dose to the patient unincreased.

22. The method of claim 18 wherein the predetermined sequence of fluences for the set of rays provides a unit fluence for one ray at a time for non-adjacent rays and including the step (c) of estimating the fluence of the rays not in the predetermined sequence.

23. The method of claim 18 wherein the predetermined sequence of test fluences includes only rays used in the treatment plan.

24. The method of claim 23 including the step of estimating the fluence of the rays not in the predetermined sequence of test fluences.

25. The method of claim 18 wherein the predetermined sequence of test fluences is repeated for a plurality of angles about the patient volume.

* * * * *

UNITED STATES PATENT AND TRADEMARK OFFICE
CERTIFICATE OF CORRECTION

PATENT NO. : 6,438,202 B1
DATED : August 20, 2003
INVENTOR(S) : Guatavo H. Olivera et al.

It is certified that error appears in the above-identified patent and that said Letters Patent is hereby corrected as shown below:

Column 1,
Line 5, before "CROSS-REFERENCE TO RELATED APPLICATIONS", insert:
-- This invention was made with United States government support awarded by the following agencies: NIH Grant Nos. CA48902; CA14520. The United States has certain rights in this invention. --

Signed and Sealed this

Second Day of March, 2004

JON W. DUDAS
*Acting Director of the United States Patent and Trademark Office*